United States Patent
Iwanaga (10) Patent No.: US 9,142,385 B1
(45) Date of Patent: Sep. 22, 2015

(54) CHARGED PARTICLE BEAM TREATMENT APPARATUS AND METHOD OF ADJUSTING PATH LENGTH OF CHARGED PARTICLE BEAM

(71) Applicant: SUMITOMO HEAVY INDUSTRIES, LTD., Tokyo (JP)

(72) Inventor: Shinji Iwanaga, Niihama (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/658,309

(22) Filed: Mar. 16, 2015

(30) Foreign Application Priority Data

Mar. 20, 2014 (JP) .................. 2014-058515

(51) Int. Cl.
| | |
|---|---|
| H05H 7/12 | (2006.01) |
| G21K 5/04 | (2006.01) |
| G21K 1/00 | (2006.01) |
| H01J 33/00 | (2006.01) |
| A61N 5/00 | (2006.01) |
| H01J 37/304 | (2006.01) |
| H01J 37/30 | (2006.01) |
| H01J 37/147 | (2006.01) |

(52) U.S. Cl.
CPC ............ *H01J 37/304* (2013.01); *H01J 37/1472* (2013.01); *H01J 37/3007* (2013.01); *H01J 2237/152* (2013.01); *H01J 2237/30472* (2013.01)

(58) Field of Classification Search
CPC .................... A61N 2005/1087; A61N 5/1043; A61N 5/1048; A61N 5/1065; A61N 5/1077; H05H 7/04; H05H 13/04; H05H 7/12; H05H 2277/11; G21K 1/093

USPC ............ 250/505.1, 492.1, 493.1; 378/16, 64, 378/65; 315/500, 111, 61
See application file for complete search history.

(56) References Cited

U.S. PATENT DOCUMENTS

| | | | | |
|---|---|---|---|---|
| 5,986,274 | A | * 11/1999 | Akiyama et al. | 250/492.3 |
| 2009/0309520 | A1 | * 12/2009 | Balakin | 315/503 |
| 2009/0314961 | A1 | * 12/2009 | Balakin | 250/492.3 |
| 2010/0207552 | A1 | * 8/2010 | Balakin | 315/503 |

FOREIGN PATENT DOCUMENTS

| | | |
|---|---|---|
| JP | 2003-033049 A | 1/2003 |
| JP | 2011-191184 A | 9/2011 |

* cited by examiner

*Primary Examiner* — Nikita Wells
(74) *Attorney, Agent, or Firm* — Squire Patton Boggs (US) LLP (57) ABSTRACT

A charged particle beam treatment apparatus includes: an accelerator configured to emit a charged particle beam by accelerating charged particles; an irradiation portion configured to irradiate an irradiation object with the charged particle beam through a scanning method; a transport line configured to transport the charged particle beam emitted from the accelerator to the irradiation portion; an energy adjusting portion configured to adjust energy of the charged particle beam; an electromagnet which is provided in the irradiation portion or the transport line; an electromagnet power source which is connected to the electromagnet; and a control portion. Semiconductors are connected between the electromagnet power source and the electromagnet in series. When switching a layer of the irradiation object to be irradiated with the charged particle beam, the control portion reduces the energy of the charged particle beam by controlling the energy adjusting portion and increases a resistance of the semiconductors.

4 Claims, 7 Drawing Sheets

CHARGED PARTICLE BEAM TREATMENT APPARATUS AND METHOD OF ADJUSTING PATH LENGTH OF CHARGED PARTICLE BEAM

RELATED APPLICATIONS

Priority is claimed to Japanese Patent Application No. 2014-058515, filed Mar. 20, 2014, the entire content of which is incorporated herein by reference.

BACKGROUND

1. Technical Field

Certain embodiments of the invention relate to a charged particle beam treatment apparatus and a method of adjusting the path length of a charged particle beam.

2. Description of Related Art

In the related art, for example, a scanning type charged particle beam treatment apparatus disclosed in the related art is known as a charged particle beam treatment apparatus which performs a treatment by irradiating an irradiation object with a charged particle beam. In the related art, there is a disclosure of a charged particle beam treatment apparatus which irradiates one layer which is set in the irradiation object with a charged particle beam along a scanning pattern, and irradiates a next layer with the charged particle beam by changing energy of the charged particle beam when the irradiation of the one layer with the charged particle beam is finished.

SUMMARY

According to an embodiment of the invention, there is provided a charged particle beam treatment apparatus including: an accelerator configured to emit a charged particle beam by accelerating charged particles; an irradiation portion configured to irradiate an irradiation object with the charged particle beam through a scanning method; a transport line configured to transport the charged particle beam emitted from the accelerator to the irradiation portion; an energy adjusting portion which adjusts configured to adjust energy of the charged particle beam; an electromagnet which is provided in the irradiation portion or the transport line; an electromagnet power source which is connected to the electromagnet; and a control portion. Semiconductors are connected between the electromagnet power source and the electromagnet in series. When switching a layer of the irradiation object to be irradiated with the charged particle beam, the control portion reduces the energy of the charged particle beam by controlling the energy adjusting portion and increases a resistance of the semiconductors.

According to another embodiment of the invention, there is provided a method of adjusting a path length of a charged particle beam in which the path length of the charged particle beam which is emitted by an irradiation portion is adjusted using the charged particle beam treatment apparatus. The apparatus includes an accelerator which emits the charged particle beam by accelerating charged particles; the irradiation portion which irradiates an irradiation object with the charged particle beam through a scanning method; the irradiation portion which irradiates an irradiation object with the charged particle beam through a scanning method; an energy adjusting portion which adjusts energy of the charged particle beam; an electromagnet which is provided in the irradiation portion or the transport line; and an electromagnet power source which is connected to the electromagnet. The method includes, reducing the energy of the charged particle beam by controlling the energy adjusting portion and increasing a resistance of semiconductors connected between the electromagnet power source and the electromagnet in series, when switching a layer of the irradiation object to be irradiated with the charged particle beam.

DETAILED DESCRIPTION

In a charged particle beam treatment apparatus, it is necessary to reduce the irradiation time in order to reduce a burden on a patient during treatment. However, in the above-described charged particle beam treatment apparatus in the related art, there is still room for improvement in the time required for switching an excitation amount with respect to an electromagnet when switching a layer to be irradiated with a charged particle beam.

It is desirable to reduce the switching time when switching a layer to be irradiated with a charged particle beam and to reduce the time for charged particle beam treatment.

In the charged particle beam treatment apparatus according to the embodiment of the invention, when switching a layer of an irradiation object to be irradiated with the charged particle beam, a control portion reduces energy of the charged particle beam by controlling an energy adjusting portion and shortens a path length of the charged particle beam. At this time, the energy of the charged particle beam decreases, and therefore, it is necessary to reduce an electric current which is made to flow to the electromagnet by an electromagnet power source. In the embodiment of the invention, when switching a layer of the irradiation object to be irradiated with the charged particle beam, the control portion reduces the energy of the charged particle beam by controlling the energy adjusting portion and increases a resistance of semiconductors connected between the electromagnet power source and the electromagnet in series. The semiconductors can increase a constant during loading by increasing the resistance of the semiconductors at a necessary timing when reducing an electric current to the electromagnet, and therefore, it is possible to reduce the time required for reducing the electric current. That is, it is possible to reduce the switching time when switching a layer to be irradiated with the charged particle beam and to reduce the time for charged particle beam treatment.

In the charged particle beam treatment apparatus according to the embodiment of the invention, the energy adjusting portion may be provided between the accelerator and the irradiation portion, and the electromagnet may include at least a converging electromagnet or a deflecting electromagnet which is arranged in the transport line. Accordingly, it is possible to reduce the time required for reducing the electric current with respect to the converging electromagnet or the deflecting electromagnet when switching a layer.

In the charged particle beam treatment apparatus according to the embodiment of the invention, the accelerator may be a synchrotron, the energy adjusting portion may be provided within the accelerator, and the electromagnet may include at least a converging electromagnet or a deflecting electromagnet which is arranged in the transport line. Accordingly, it is possible to reduce the time required for reducing the electric current with respect to the converging electromagnet or the deflecting electromagnet when switching a layer.

According to the method of adjusting a path length of a charged particle beam according to the embodiment of the invention, it is possible to obtain the same action and effect as those of the above-described charged particle beam treatment apparatus.

Hereinafter, embodiments of the invention will be described in detail with reference to the accompanying drawings. The terms "upstream" and "downstream" respectively mean an upstream (accelerator side) and a downstream (patient side) of an emitted charged particle beam.

Figure 1:
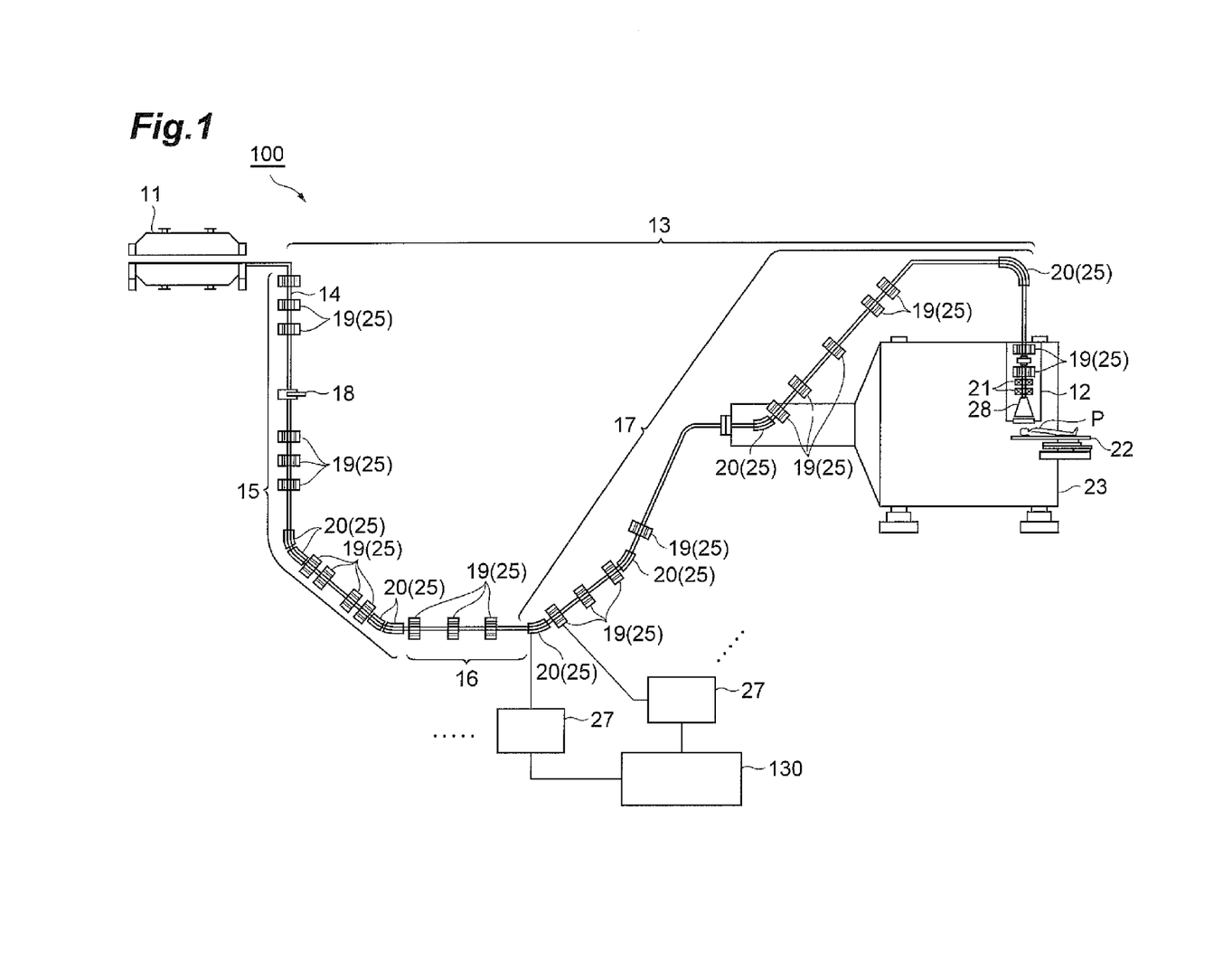
FIG. 1 is a schematic view showing a charged particle beam irradiation apparatus according to an embodiment of the invention.

As shown in FIG. 1, a charged particle beam treatment apparatus 100 is an apparatus used to treat cancer or the like through radiation therapy, and includes an accelerator 11 which emits a charged particle beam by accelerating charged particles; an irradiation nozzle 12 (irradiation portion) which irradiates an irradiation object with the charged particle beam; a beam transport line 13 (transport line) which transports the charged particle beam emitted from the accelerator 11 to the irradiation nozzle 12; a degrader (energy adjusting portion) 18 which is provided in the beam transport line 13 and adjusts a path length of the charged particle beam by reducing energy of the charged particle beam; a plurality of electromagnets 25 which are provided in the irradiation nozzle 12 and the beam transport line 13; electromagnet power sources 27 which are provided so as to correspond to the plurality of electromagnets 25; and a control portion 130 which controls the entirety of the charged particle beam treatment apparatus 100. In the present embodiment, a cyclotron is employed as the accelerator 11, but the embodiment of the invention is not limited thereto, and other generators, such as a synchrotron, a synchrocyclotron, and a linac, which generate a charged particle beam, may be used.

In the charged particle beam treatment apparatus 100, irradiation of a tumor (irradiation object) of a patient P on a treatment table 22 with a charged particle beam emitted from the accelerator 11 is performed. The charged particle beam is a beam in which particles having electrical charges are accelerated at a high speed, and examples thereof include a proton beam, heavy particle (heavy ion) beam, or the like. The charged particle beam treatment apparatus 100 according to the present embodiment is an apparatus performing irradiation of an irradiation object with a charged particle beam through a so-called scanning method, and virtually divides (slices) the irradiation object in a depth direction and irradiates an irradiation range on a layer with a charged particle beam for each sliced plane (layer) (for example, refer to FIGS. 3A and 3B).

Examples of the irradiation method using the scanning method include a spot scanning irradiation and raster scanning irradiation. The spot scanning irradiation has a system in which when irradiation on a spot, as an irradiation range, is completed, the irradiation on the spot with a beam (charged particle beam) is stopped once, and irradiation on a next spot is performed after preparation for irradiating the next spot is finished. In contrast, the raster scanning irradiation has a system in which beam irradiation of an irradiation range on an identical layer is continuously performed without stopping the irradiation in the middle of the irradiation. In this manner, in the raster scanning irradiation, beam irradiation of the irradiation range on the identical layer is continuously performed, and therefore, the irradiation range is not configured to have a plurality of spots unlike the spot scanning irradiation.

The irradiation nozzle 12 is attached to the inside of a rotary gantry 23, which is rotatable around the treatment table 22 by 360 degrees, and is set to be movable at an arbitrary rotational position using the rotary gantry 23. The irradiation nozzle 12 includes a converging electromagnet 19 (details of which will be described later), a scanning electromagnet 21, and a vacuum duct 28. The scanning electromagnet 21 is provided in the irradiation nozzle 12. The scanning electromagnet 21 has an X-direction scanning electromagnet which scans a charged particle beam in an X-direction in a plane intersecting an irradiation direction of the charged particle beam, and a Y-direction scanning electromagnet which scans a charged particle beam in a Y-direction intersecting the X-direction in the plane intersecting the irradiation direction of the charged particle beam. In addition, the charged particle beam scanned by the scanning electromagnet 21 is deflected in the X-direction and/or Y-direction, and therefore, the diameter of the vacuum duct 28 further on a downstream side than the scanning electromagnet increases toward the downstream side.

The beam transport line 13 has a vacuum duct 14 through which a charged particle beam passes. The inside of the vacuum duct 14 is maintained in a vacuum state, and therefore, scattering of charged particles which constitute the charged particle beam due to the air or the like is suppressed during the transporting.

In addition, the beam transport line 13 has an energy selection system (ESS) 15 which selectively picks up a charged particle beam having an energy width narrower than a predetermined energy width from a charged particle beam having a predetermined energy width which is emitted from the accelerator 11; a beam transport system (BTS) 16 which transports the charged particle beam having a energy width which is selected by the ESS 15 in a state in which the energy is kept; and a gantry transport system 17 (GTS) which transports the charged particle beam from the BTS 16 to the rotary gantry 23.

The degrader 18 adjusts the path length of the charged particle beam by reducing the energy of the charged particle beam passing therethrough. The depth from a body surface of a patient to a tumor as an irradiation object varies depending on the patient, and therefore, it is necessary to adjust the path length which is a depth to which the charged particle beam reaches when irradiating the patient with the charged particle beam. The degrader 18 performs the adjustment such that the charged particle beam properly reaches the irradiation object at a predetermined depth in the body of a patient by adjusting the energy of the charged particle beam emitted from the accelerator 11 at a constant energy. Such adjustment of the energy of the charged particle beam using the degrader 18 is performed for each of the sliced layers of the irradiation object.

A plurality of electromagnets 25 are provided in the beam transport line 13, and adjust the charged particle beam such that the beam transport line 13 can transport the charged particle beam using a magnetic field. As the electromagnets 25, converging electromagnets 19 which converge a beam diameter of the charged particle beam during the transporting, and deflecting electromagnets 20 which deflect the charged particle beam are employed. In some cases, the converging electromagnets 19 and the deflecting electromagnets 20 are described as the electromagnets 25 without distinguishing them. In addition, a plurality of the electromagnets 25 are provided further on a downstream side than the degrader 18 at least in the beam transport line 13. However, in the present embodiment, the electromagnets 25 are also provided further on an upstream side than the degrader 18. Here, the converging electromagnets 19 are provided as the electromagnets 25 on the upstream side of the degrader 18 in order to converge the beam diameter of the charged particle beam before the adjustment of the energy using the degrader 18. The total number of the electromagnets 25 can be flexibly changed depending on the length or the like of the beam transport line 13, and examples thereof include about 10 to 40. Only some of the electromagnet power sources 27 are described in FIG. 1. However, in reality, the same number of the electromagnet power sources 27 as that of the electromagnets 25 is provided.

The position of the degrader 18 and the electromagnets 25 in the beam transport line 13 is not particularly limited, but in the present embodiment, the degrader 18, the converging electromagnets 19, and the deflecting electromagnets 20 are provided in the ESS 15. In addition, the converging electromagnets 19 are provided in the BTS 16, and the converging electromagnets 19 and the deflecting electromagnets 20 are provided in the GTS 17. The degrader 18 is provided in the ESS 15 between the accelerator 11 and the rotary gantry 23, and more specifically, the degrader 18 is provided further on the accelerator 11 side (upstream side) than the rotary gantry 23 in the ESS 15.

The electromagnet power sources 27 generate amagnetic field of the electromagnets 25 by supplying an electric current to the corresponding electromagnets 25. The electromagnet power sources 27 can adjust the intensity of the magnetic field of the corresponding the electromagnets 25 by adjusting the electric current to be supplied to the corresponding electromagnets 25. The electromagnet power sources 27 adjust the electric current to be supplied to the electromagnets 25 depending on a signal from the control portion 130 (details will be described later). The electromagnet power sources 27 are provided so as to correspond to the electromagnets 25 one to one. That is, the same number of the electromagnet power sources 27 as that of the electromagnets 25 is provided.

The relationship between depth of each layer of the irradiation object and the electric current supplied to the electromagnets 25 is as follows. That is, energy of the charged particle beam required irradiating each layer with the charged particle beam is determined from the depth of each layer, and the amount of adjusting the energy using the degrader 18 is determined. Here, when the energy of the charged particle beam changes, the intensity of the magnetic field required for deflating and converging the charged particle beam also changes. Accordingly, the electric current to be supplied to the electromagnets 25 is determined such that the intensity of the magnetic field of the electromagnets 25 becomes an intensity corresponding to the amount of adjusting the energy using the degrader 18.

Figure 2:
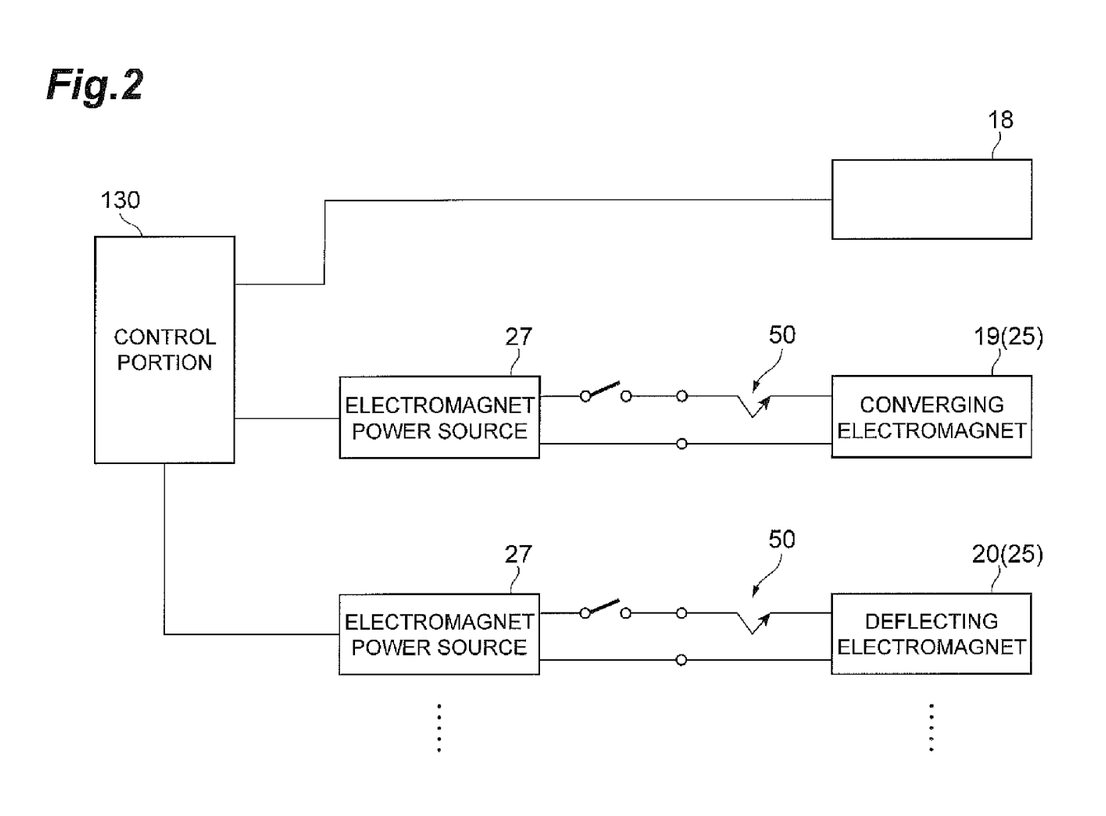
FIG. 2 is a block configuration view showing a configuration around a control portion and an electromagnet.

Next, the control portion 130 and the electromagnet power sources 27 will be described in detail with reference to FIG. 2 as well. Only some of the electromagnet power sources 27 are described in FIG. 2. However, in reality, the same number of the electromagnet power sources 27 corresponding to that of the electromagnets 25 provided in the charged particle beam treatment apparatus 100 is provided.

Figure 3A:
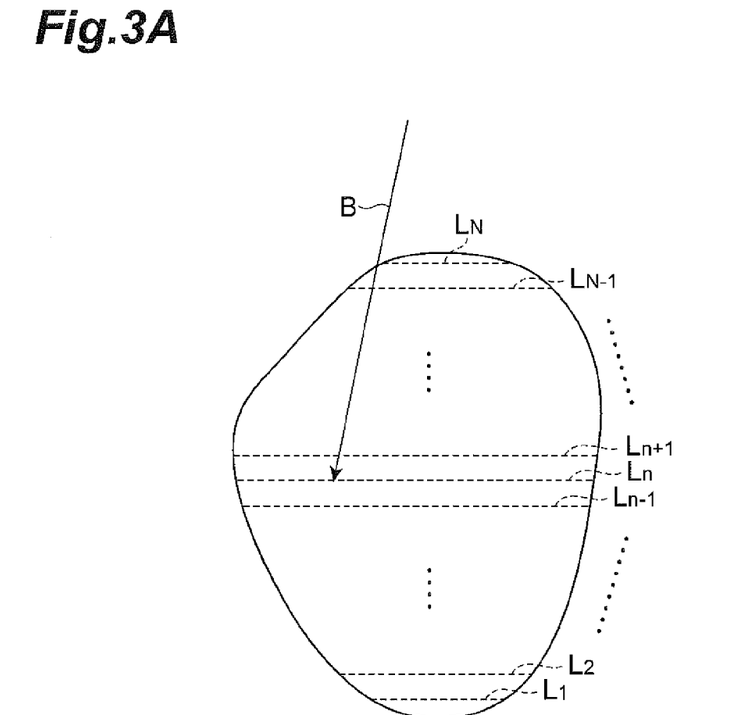
FIGS. 3A and 3B are views showing irradiation images of a charged particle beam.
Figure 3B:
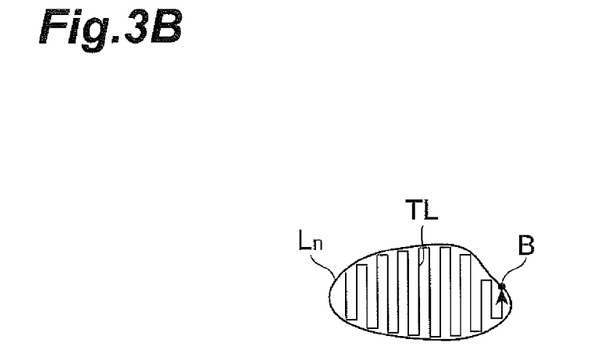

The control portion 130 controls irradiation of an irradiation object with a charged particle beam emitted from the accelerator 11. The control portion 130 irradiates a layer set in the irradiation object with the charged particle beam along a predetermined scanning pattern by controlling the scanning electromagnet 21. In addition, the control portion 130 adjusts the energy of the charged particle beam by controlling the degrader 18 and adjusts the path length of the charged particle beam. Accordingly, to the control portion 130 can switch the layer to be irradiated with the charged particle beam. Here, irradiation images of the charged particle beam in accordance with the control of the control portion 130 will be described with reference to FIGS. 3A and 3B. FIG. 3A shows an irradiation object virtually sliced into a plurality of layers in a depth direction, and FIG. 3B shows a scanning image of the charged particle beam in one layer as seen from the irradiation direction of the charged particle beam.

As shown in FIG. 3A, the irradiation object is virtually sliced into the plurality of layers in the depth direction, and in the present example, is virtually sliced into N layers including layer $L_1$, layer $L_2$, ... layer $L_{n-1}$, layer $L_n$, layer $L_{n+1}$, ... layer $L_{N-1}$, and layer $L_N$ in order from a deeper layer (having a long path length of a charged particle beam B). In addition, as shown in FIG. 3B, a plurality of irradiation spots of the layer $L_n$ are irradiated with an charged particle beam B while drawing a beam orbit TL. That is, the charged particle beam emitted from the irradiation nozzle 12 by being controlled by the control portion 130 moves on the beam orbit TL. In addition, when the irradiation of the one layer $L_n$ is finished, the control portion 130 reduces the energy of the charged particle beam by controlling the degrader 18 and shortens the path length of the charged particle beam B. Accordingly, the layer $L_{n+1}$ which is a one step upper layer is irradiated with the charged particle beam B.

Semiconductors (transistors) 50 are connected between an electromagnet power source 27 and an electromagnet 25 in series. The control portion 130 can control the resistance in the semiconductors 50 by controlling the electric current to be input to the semiconductors 50. Here, when changing the layer to be irradiated with a charged particle beam, the control portion 130 reduces the energy of the charged particle beamby controlling the degrader 18 in order to shorten the path length. At this time, the control portion 130 reduces the electric current to be input to the electromagnets 25 from the electromagnet power sources 27 in order to reduce the excitation amount to the electromagnets 25 corresponding to the reduction of the energy of the charged particle beam. At this time, the control portion 130 increases the resistance of the semiconductors 50 in order to absorb the energy remaining in the electromagnets 25.

Figure 4:
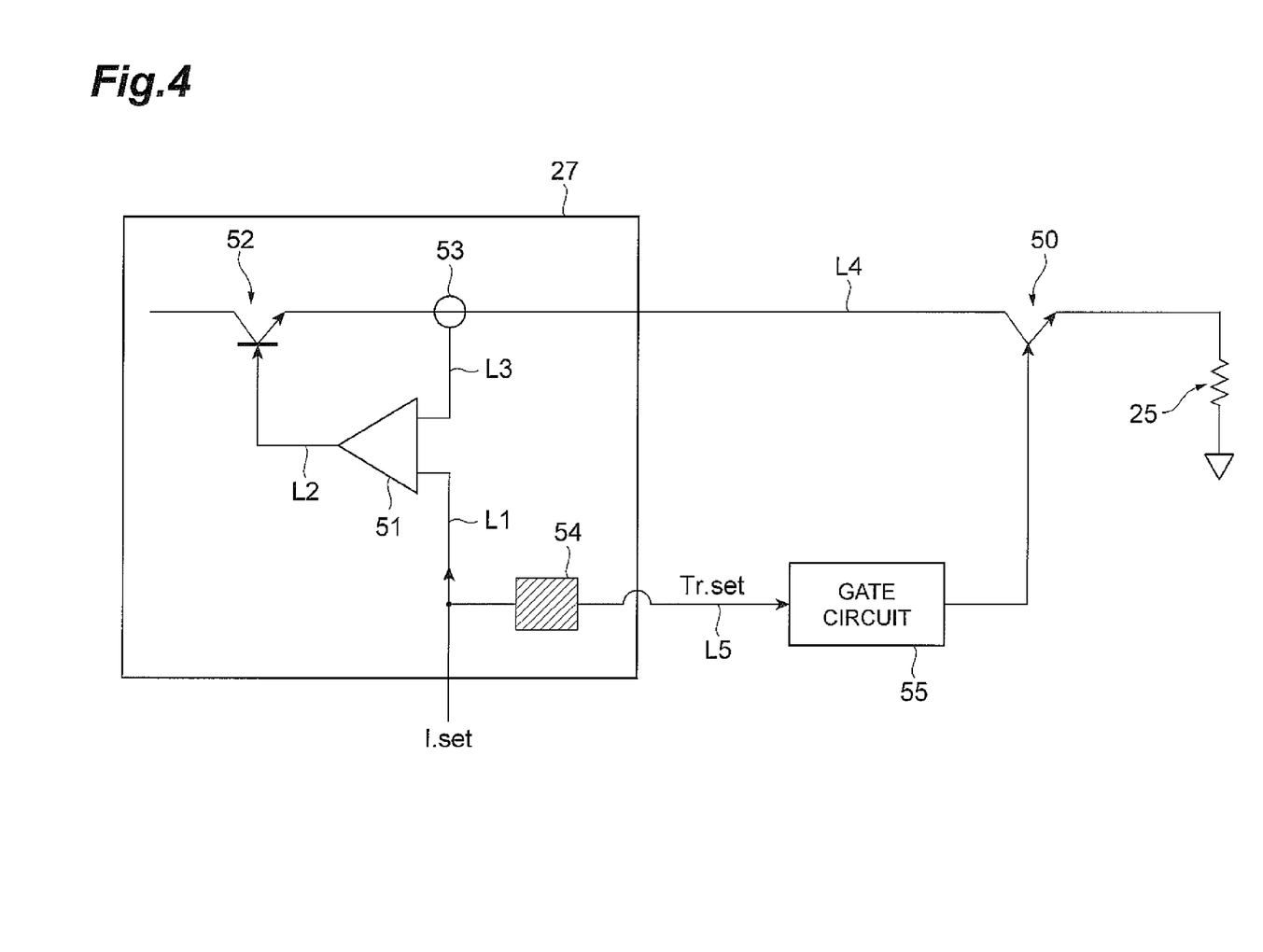
FIG. 4 is a configuration view showing a circuit configuration around an electromagnet power source and semiconductors.

Next, circuit configuration around an electromagnet power source 27 and semiconductors 50 will be described in detail with reference to FIG. 4. As shown in FIG. 4, in the electromagnet power source 27, an electric current which is set to an electric current setting value I.set passes through a line L1, and flows through a line L4 via an electric current feedback portion 51, a line L2, and the semiconductor 52. The semiconductor 50 is provided in the line L4 as a resistance, and the electric current flows to the electromagnet 25 via the semiconductor 50. An electric current monitor 53 is provided in the line L4 and performs electric current feedback by transmitting a signal to an electric current feedback portion 51 via the line L3 by detecting the electric current. Meanwhile, a line L5 is branched from the line L1, and a signal generating circuit 54 and a gate circuit 55 are provided in the line L5. The line L5 is connected to the semiconductor 50. In such a circuit configuration, the electric current which is set to the electric current setting value I.set flows through the line L1, and the signal generating circuit 54 generates a signal by setting a resistance setting value Tr.set corresponding to the electric current setting value I.set. In addition, the gate circuit 55 inputs the electric current corresponding to the resistance setting value Tr.set into the semiconductor 50.

Figure 5:
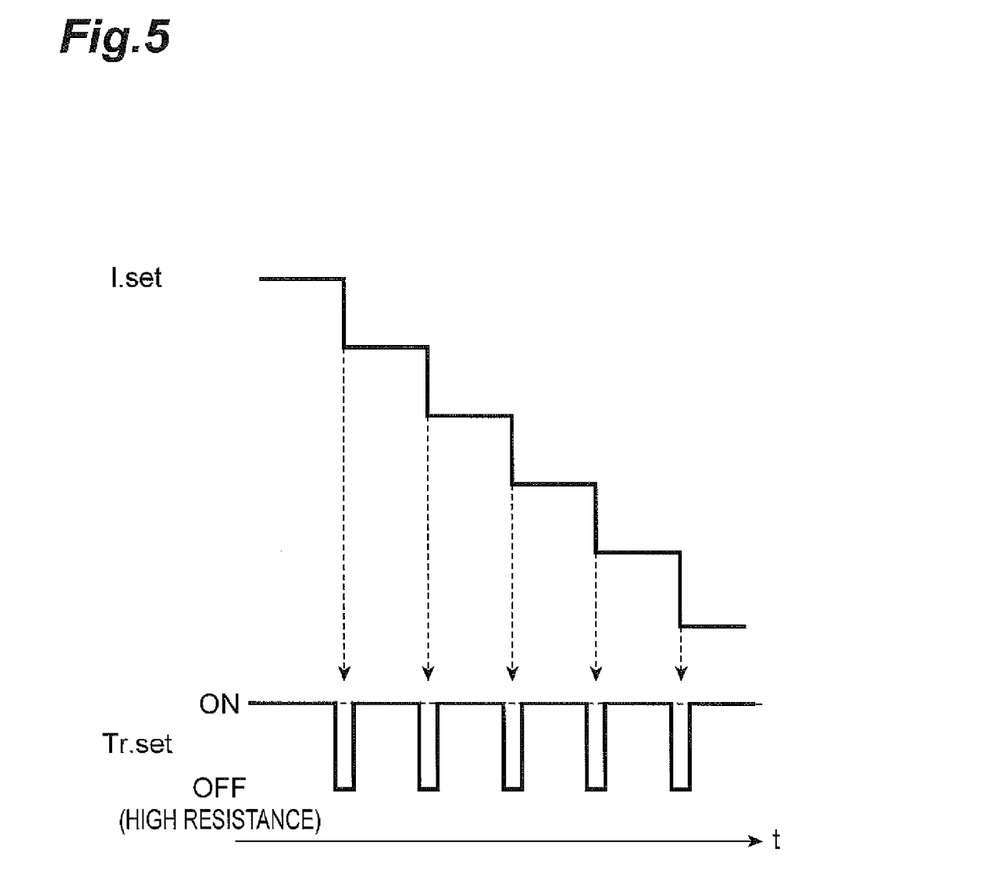
FIG. 5 is a conceptual view showing a relationship between an electric current flowing to an electromagnet and a resistance of a semiconductor.
Figure 6:
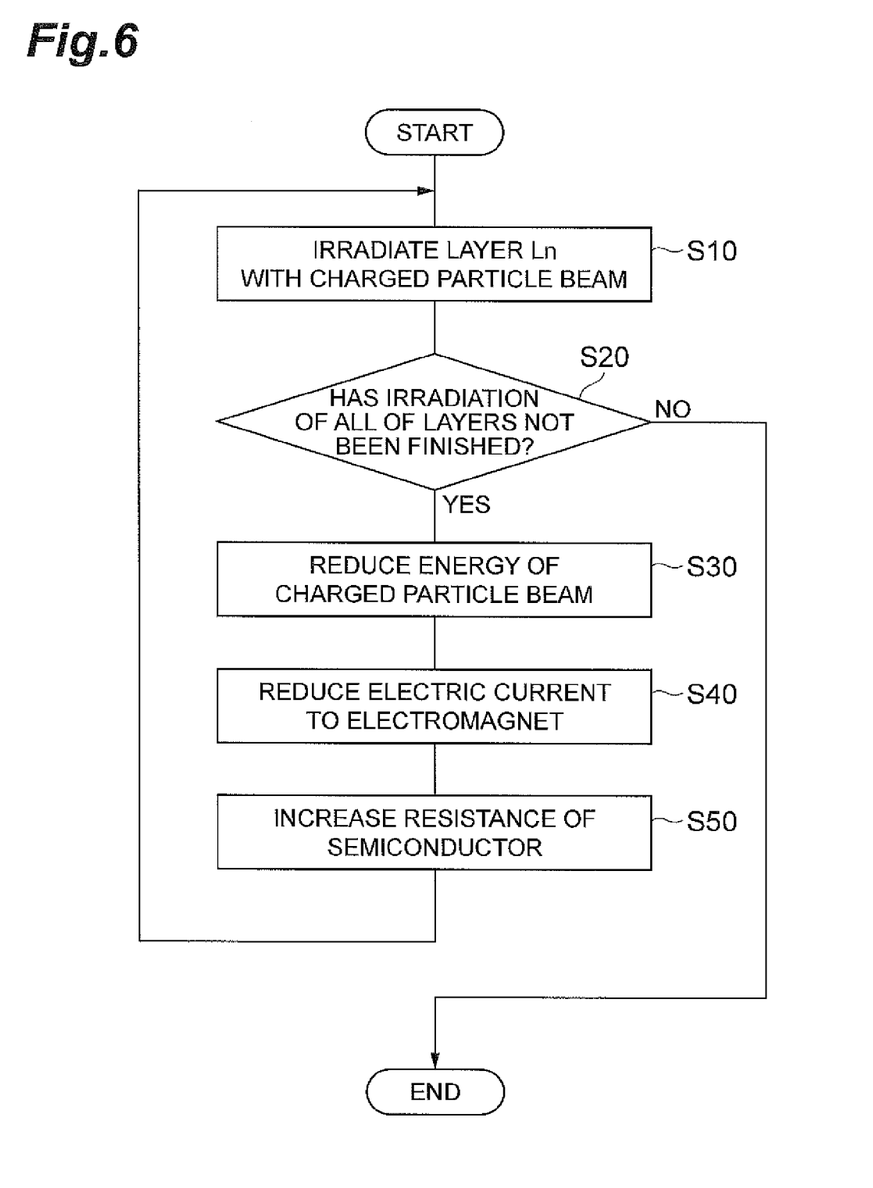
FIG. 6 is a flowchart showing the content of processing executed by a control portion of a charged particle beam treatment apparatus.

Next, a method of adjusting a path length of a charged particle beam will be described with reference to FIGS. 5 and 6. FIG. 5 is a conceptual view showing a relationship between an electric current flowing to an electromagnet 25 and a resistance of a semiconductor 50. FIG. 6 is a flowchart showing the content of processing executed by the control portion 130 of the charged particle beam treatment apparatus 100. As shown in FIG. 6, the control portion 130 irradiates the layer $L_n$ with a charged particle beam along the scanning pattern by controlling the irradiation nozzle 12 (step S10). At this time, the control portion 130 makes a constant electric current (that is, the electric current setting value I.set is constant) flow to an electromagnet 25 by controlling an electromagnet power source 27, and sets the resistance setting value Tr.set to ON such that the resistance of the semiconductor 50 becomes low (refer to FIG. 5). Next, the control portion 130 determines whether the irradiation of all of the layers $L_1$ to $L_N$ is not finished (step S20). When it is determined that the irradiation of all of the layers $L_1$ to $L_N$ is not finished, the control portion 130 performs a process of switching the layer to be irradiated.

Specifically, the control portion 130 reduces the energy of the charged particle beam by controlling the degrader 18 (step S30). In addition, the control portion 130 reduces the electric current flowing to the electromagnet 25 by reducing the electric current setting value I.set by controlling the electromagnet power source 27 (step S40). At this time, the control portion 130 sets the resistance setting value Tr.set to OFF to increase the resistance of the semiconductor 50 (step S50). Accordingly, the semiconductor 50 absorbs the energy remaining in the electromagnet 25. In this manner, the electric current setting value I.set draws a waveform decreasing stepwise by repeating the switching of the layer to be irradiated. In addition, the resistance setting value Tr.set is set to ON when the electric current setting value I.set is set to a constant value, and is locally set to OFF only when the electric current setting value I.set is reduced. When the irradiation of all of the layers $L_1$ to $L_N$ with the charged particle beam is finished, the state is determined to be No in S20, and the process shown in FIG. 6 is finished.

Next, the action and effect of the charged particle beam treatment apparatus 100 according to the present embodiment will be described.

In the charged particle beam treatment apparatus 100, when switching the layer of an irradiation object to be irradiated with a charged particle beam, the control portion 130 reduces energy of the charged particle beam by controlling the degrader 18 and shortens the path length of the charged particle beam. At this time, the energy of the charged particle beam is reduced, and therefore, it is also necessary to reduce an electric current which is made to flow to the electromagnet 25 by an electromagnet power source 27. It is necessary to increase a constant during loading in order to accelerate the speed of the electric current reduction of the electromagnet 25. A configuration is considered in which resistors are provided between the electromagnet power sources 27 and electromagnets 25 in series and the energy of the load (electromagnets 25) is consumed by the resistors. In such a configuration, there is a problem in that the resistance of the resistors becomes extremely large and large resistance acts also when it is unnecessary to apply the resistance (when emitting the charged particle beam), and therefore, a large amount of power is required. In addition, when regenerating the energy of the electromagnets 25 by providing condensers between the electromagnet power sources 27 and the electromagnets 25 in series, there is a problem in that inductance of the electromagnets 25 increases, and therefore, it is necessary to provide extremely large condensers.

In contrast, in the present embodiment, when switching a layer of an irradiation object to be irradiated with a charged particle beam, the control portion 130 reduces energy of the charged particle beam by controlling the degrader 18 and increases a resistance of the semiconductors 50 connected between the electromagnet power sources 27 and the electromagnets 25 in series. The semiconductors 50 can increase a constant during loading by increasing the resistance of the semiconductors at a necessary timing when reducing an electric current to the electromagnets 25, and therefore, it is possible to reduce the time required for reducing the electric current. That is, it is possible to reduce the switching time when switching a layer to be irradiated with the charged particle beam and to reduce the time for charged particle beam treatment. For example, it is possible to switch the layer at about 100 milliseconds in the charged particle beam treatment apparatus 100 according to the present embodiment whereas about 2 seconds are required for switching the layer in the charged particle beam treatment apparatus in the related art. In general, several tens of the layers are provided, and therefore, it is possible to greatly reduce the total time for changing the layers. As a result, it is possible to greatly reduce the time for charged particle beam treatment. In addition, the control portion 130 can make the resistance of the semiconductors 50 small at a timing when it is unnecessary to increase the resistance, and therefore, there is no problem when arranging the resistors or the condensers.

In the charged particle beam treatment apparatus 100 according to the present embodiment, the degrader 18 is provided between the accelerator 11 and the irradiation nozzle 12, and the electromagnet 25 includes at least the converging electromagnet 19 or the deflecting electromagnet 20 which is arranged in the beam transport line 13. Accordingly, it is possible to reduce the time required for reducing the electric current with respect to the converging electromagnet 19 or the deflecting electromagnet 20 when switching a layer.

The present invention is not limited to the above-described embodiment. For example, the circuit configuration around the electromagnet power source is not limited to that shown in FIG. 4. In addition, fixed irradiation may be performed by fixing the irradiation nozzle without using the rotary gantry 23. In addition, another degrader may be provided at a position closer to the rotary gantry than a cyclotron instead of the degrader 18. In addition, the accelerator 11 may be a synchrotron and the degrader 18 may be provided in the accelerator 11.

Figure 7:
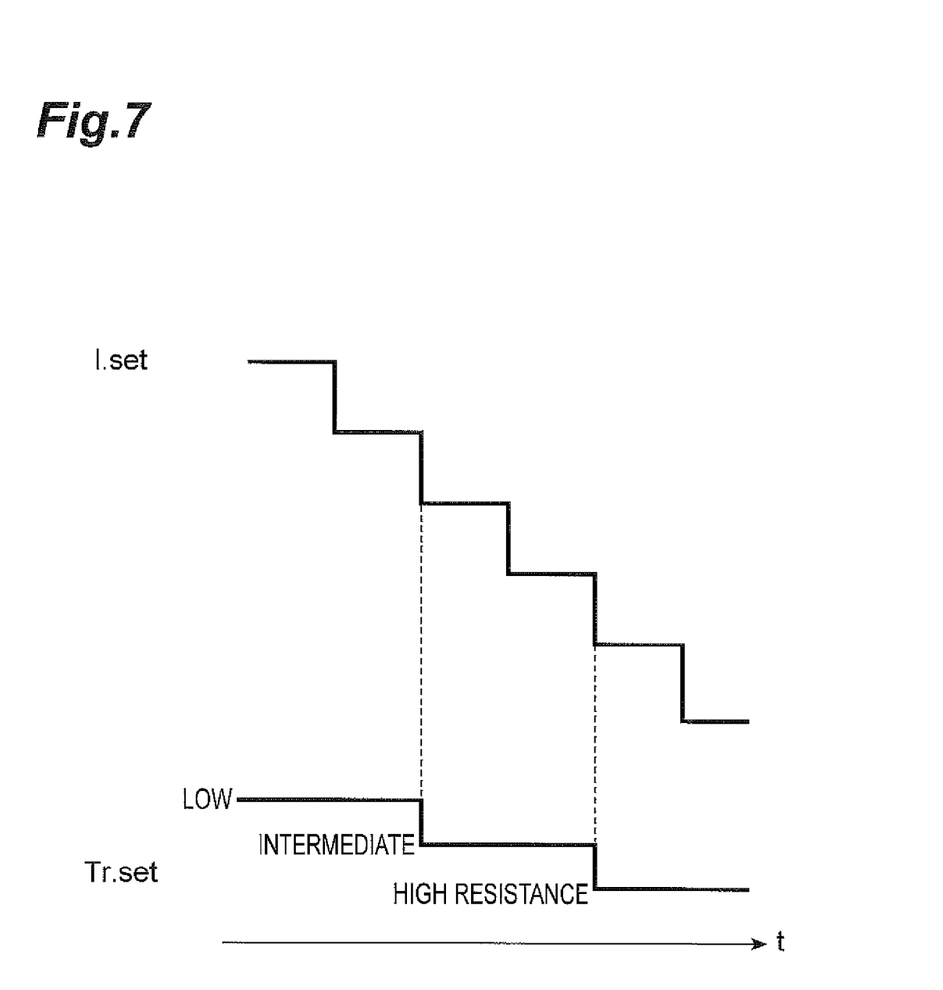
FIG. 7 is a conceptual view showing a relationship between an electric current flowing to an electromagnet and a resistance of a semiconductor.

In addition, the pattern of the resistance of the semiconductors 50 is not limited to that shown in FIG. 5. For example, a pattern of resistance shown in FIG. 7 may be employed. As shown in FIG. 7, the resistance of the semiconductors 50 may be set to be low in a state where the electric current flowing to the electromagnets 25 is high, the resistance of the semiconductors 50 may be set to an intermediate value at a timing when the electric current decreases several steps, and the resistance of the semiconductors 50 may be set to be high at a timing when the electric current decreases more several steps.

It should be understood that the invention is not limited to the above-described embodiment, but may be modified into various forms on the basis of the spirit of the invention. Additionally, the modifications are included in the scope of the invention.

What is claimed is:

1. A charged particle beam treatment apparatus comprising:
    an accelerator configured to emit a charged particle beam by accelerating charged particles;
    an irradiation portion configured to irradiate an irradiation object with the charged particle beam through a scanning method;
    a transport line configured to transport the charged particle beam emitted from the accelerator to the irradiation portion;
    an energy adjusting portion configured to adjust energy of the charged particle beam;
    an electromagnet which is provided in the irradiation portion or the transport line;
    an electromagnet power source which is connected to the electromagnet; and
    a control portion,
    wherein semiconductors are connected between the electromagnet power source and the electromagnet in series, and
    when adjusting a path length which is a depth to which the charged particle beam reaches when irradiating the irradiation object with the charged particle beam by controlling the energy adjusting portion and increases a resistance of the semiconductors.

2. The charged particle beam treatment apparatus according to claim 1,
    wherein the energy adjusting portion is provided between the accelerator and the irradiation portion, and
    wherein the electromagnet includes at least a converging electromagnet or a deflecting electromagnet which is arranged in the transport line.

3. The charged particle beam treatment apparatus according to claim 1,
    wherein the accelerator is a synchrotron,
    wherein the energy adjusting portion is provided within the accelerator, and
    wherein the electromagnet includes at least a converging electromagnet or a deflecting electromagnet which is arranged in the transport line.

4. A method of adjusting a path length of a charged particle beam in which the path length of the charged particle beam which is emitted by an irradiation portion is adjusted using the charged particle beam treatment apparatus,
    the apparatus including
    an accelerator which emits the charged particle beam by accelerating charged particles,
    the irradiation portion which irradiates an irradiation object with the charged particle beam through a scanning method,
    a transport line which transports the charged particle beam emitted from the accelerator to the irradiation portion,
    an energy adjusting portion which adjusts energy of the charged particle beam,
    an electromagnet which is provided in the irradiation portion or the transport line, and
    an electromagnet power source which is connected to the electromagnet,
    the method comprising
    reducing the energy of the charged particle beam by controlling the energy adjusting portion and increasing a resistance of semiconductors connected between the electromagnet power source and the electromagnet in series, when adjusting a path length which is a depth to which the charged particle beam reaches when irradiating the irradiation object with the charged particle beam.

* * * * *